United States Patent [19]
Kirsch

[11] 4,167,179
[45] Sep. 11, 1979

[54] PLANAR RADIOACTIVE SEED IMPLANTER

[76] Inventor: Mark Kirsch, 716 Shadylawn Rd., Lake Forest, Chapel Hill, N.C. 27514

[21] Appl. No.: 842,391

[22] Filed: Oct. 17, 1977

[51] Int. Cl.² ............................................. A61N 5/01
[52] U.S. Cl. ....................................... 128/1.2; 128/217
[58] Field of Search .......................... 128/1.2, 253, 217

[56] References Cited
U.S. PATENT DOCUMENTS

| | | | |
|---|---|---|---|
| 1,867,624 | 7/1932 | Hoffman | 128/1.2 |
| 2,617,418 | 11/1952 | Delpico | 128/253 |
| 3,086,530 | 4/1963 | Groom | 128/253 X |
| 3,674,006 | 7/1972 | Holmer | 128/1.2 |
| 3,741,211 | 6/1973 | Vreeland, Jr. | 128/253 X |
| 3,750,653 | 8/1973 | Simon | 128/1.2 |

OTHER PUBLICATIONS

Graham, A. J., *Med. Journ. & Record*, 1925, Jul.-Dec., pp. 527-529.
Haybittle, J. L. et al., *Brit. Journ. of Radiology*, 48, No. 568, Apr. 1975, pp. 295-298.

*Primary Examiner*—Kyle L. Howell
*Attorney, Agent, or Firm*—Laff, Whitesel & Rockman

[57] ABSTRACT

A new device for inserting radioactive seeds in and around tumor volumes is based upon insertion of a planar array of seeds at fixed depth. The device uses a fixed array of hollow needles with a matching array of trochars. The result achieved using this device is the implantation of a planar array of radioactive seeds which does not depend upon the parallel insertion of individual needles.

5 Claims, 5 Drawing Figures

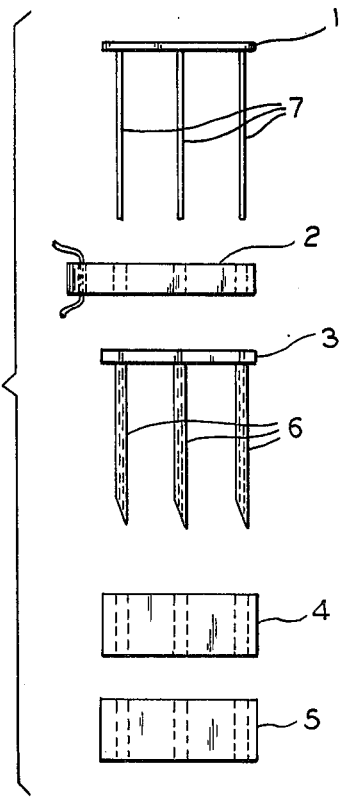
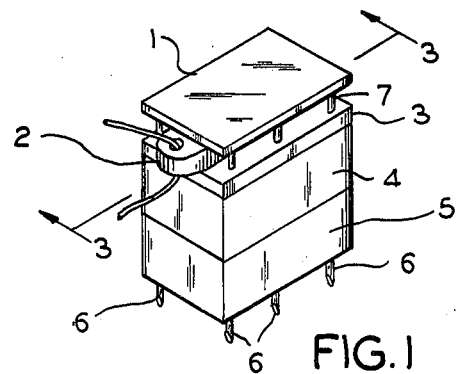
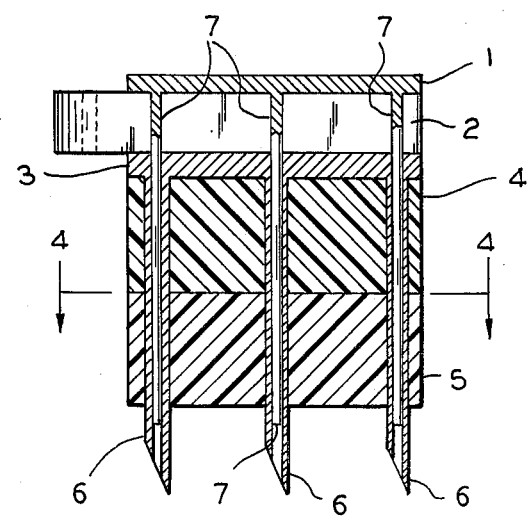
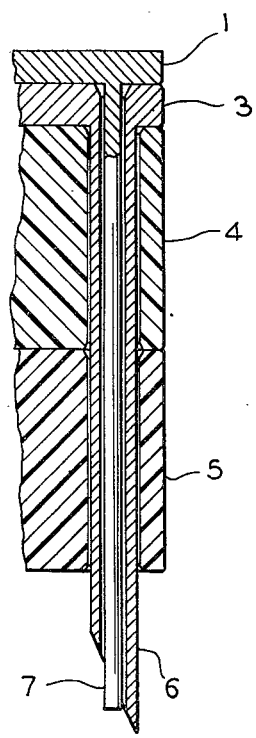
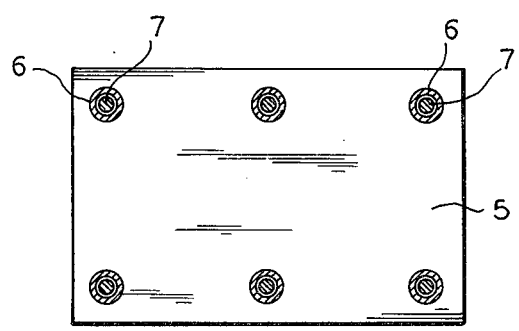

PLANAR RADIOACTIVE SEED IMPLANTER

This invention relates to a device for administering interstitial radiation therapy and more particularly, to a device for delivering a planar set of radioactive interstitial implants at a predetermined subcutaneous level. The invention provides a novel, reliable, and expedient means of utilizing radioactive implants for the treatment of malignant diseases.

Ionizing radiation is a well established mode of treatment for malignant diseases. There are essentially two ways in which such radiation may be applied to the malignant tissues; external beam therapy and the interstitial implantation of radioactive sources. Interstitial implants have over the years come to be well recognized in radiation therapy. They are used to treat small malignant growths, and are also used to deliver additional or "boost" doses to a small area after completion of the external beam therapy.

The advantages of interstitial therapy are that: (1) high doses of radiation may be delivered to small tumor volumes with a minimal destruction of the normal tissues and organs; (2) cells which are anoxic and resistant to conventional external beam therapy are much less resistant to the continuous irradiation from interstitial sources.

The disadvantages of present interstitial implant procedures are that: (1) the volume to be irradiated has to be well defined; and, (2) the operator is exposed to some radiation in the process of inserting the implant.

To overcome the problem of operator exposure, various techniques have been developed including the use of hollow tubes filled with radioactive ribbons. This is referred to as "the after loading technique". (See, e.g., *Afterloading in Radiotherapy*, DHEW Publication No. (FDA) 72-8024, BAH/DMRE 72-4 (1971)).

During the development stages of radiation therapy, radium was inserted into tumors through hollow platinum needles as a temporary implant. Later, radon filled glass or platinum seeds were used as permanent implants inserted through needles. Still later, radioactive gold became a popular material. (See, e.g., Hilaris, Kim, and Tokita, *Low Energy Radionuclides for Permanent Interstitial Implantation*, 126 American Journal of Roentgenology, Radium Therapy and Nuclear Medicine, 171–178 (January, 1976)).

In using radioactive materials for interstitial implants, it is essential that the implants be precisely distributed throughout the tumor volume. Patterson and Parker first developed rules for the distribution of the radioactive material, based on calculations for the use of radium. These rules call for a greater activity of radium to be placed at the periphery of the implanted tumor volume than in the center of the volume.

Quimby at the Memorial Hospital in New York developed another set of rules requiring that the radioactive material be evenly distributed throughout the volume. Quimby felt that high doses of radiation within the tumor volume were not a disadvantage. Following Quimby, the work of Hillaris from Memorial Hospital has led to the popularity of radioactive iodine ($^{125}$I) for permanent interstitial implants. (*Grand Rounds*, 47 Postgraduate Medicine, 226–230 (March, 1970); Kim and Hilaris, *Iodine 125 Source In Interstitial Tumor Therapy*, 123 American Journal of Roentgenology, Radium Therapy and Nuclear Medicine, 163–169 (January, 1975); U.S. Dept. H.E.W., *The Use of Iodine-125 For Interstitial Implants*, DHEW Publication (FDA) 76-8022 (November, 1975)).

An elaborate system of temporary implants has been developed in France under Pierquin at the Institute Gustav Roussie, based on the use of Irridium ($^{192}$Ir). Their experience with several thousand patients demonstrates the superiority of the use of implants. Tumors treated by Pierquin's methods established breakthroughs in curing cancer without the need of surgery. (See, e.g., Pierquin, Chassagne, Baillet, and Paine, *Clinical Observations on the Time Factor in Interstitial Radiotherapy Using* $^{192}$*Ir*, 24 Clin. Radiol. 506–509 (1973); Pierquin, Chassagne, and Cox, *Toward Consistent Local Control of Certain Malignant Tumors*, 99 Radiology, 661–667 (1971)).

To help insert the radioactive materials with precise spacing within the tumor volume, various techniques have been developed. Each is suitable for one or more of the different types of radioactive materials used. Pierquin developed various guide gutter needles for temporary implants. He and Paine also developed an afterloading technique using irridium wires which are threaded through polythene tubing to form a temporary implant. (Paine, *Modern Afterloading Methods For Interstitial Radiotherapy*, 23 Clinical Radiology, 263–272 (1972)). Techniques using stabilizers and guides have also been developed for keeping radioactive radium filled needles parallel during a temporary implant.

Permanent implants require greater accuracy in insertion. Once they are in position, they cannot be removed or adjusted. However, present apparatus available for inserting evenly spaced radioactive permanent seeds is at best crude. For example, one applicator presently available commercially requires that a set of pre-loaded needles be inserted parallel to each other into the tumor. The radioactive seeds are then held in a fixed position by a trocher inserted into the needles from the back, and the trocher is stabilized against the surface of the tumor. The outer needle is then removed, leaving a track of seeds. (Scott W. P., *Permanent Interstitial Implantation Technique Using Absorbable Spacers*, 114 American Journal of Roentgenology, Radium Therapy and Nuclear Medicine, 620–622 (March, 1972)).

When using this technique, difficulty is encountered in inserting the needles into the tumor in a truly parallel fashion. Small deviations from the parallel will result in the tips of the needles converging or diverging within the tumor, resulting in a poor spacial distribution of the seeds.

Scott has developed a needle for inserting a row of seeds which are pre-loaded into slots in the side of the needles. However, in using this technique, it is found that the $^{125}$I seeds tend to stick in the slots. Thus, the operator cannot be sure that all the seeds have unloaded into the tumor.

The Royal Marsden Hospital has developed a "Marsden Gun", which drops seeds from a cartridge into the tumor as the needle is withdrawn. Here, parallelism of the needles is still a problem. Also, only radioactive gold seeds have the uniformity necessary to fit into the cartridge and needle device. Radioactive $^{125}$I with its end welded titanium coat is too irregular for use with this gun and cannot be used in this device.

Laurence Soft Ray, a supplier of radioactive Iodine seeds in America has suggested that the $^{125}$I seeds can be pre-loaded into braided absorbable suture material and then sewn into the tumor. However, parallelism of the threads is still a problem with this method.

The present invention has as a primary objective the provision of a device which will overcome the inadequacies of present devices for implanting radioactive seeds in tumor volumes. A more particular object is to provide a device which is quick, easy, accurate and reliable for overcoming the problems of parallel insertion of radioactive seeds. Yet another objective of this invention is to provide a means for inserting a fixed array of seeds in a planar distribution at a predetermined depth below the skin surface.

The planar seed applicator which is the subject of the present invention consists of an array of hollow needles with a matching array of trochars. Using this device, it is possible to insert the seeds in planes at a fixed depth from the surface. Each plane has a fixed spacing of the seeds on the plane and the height of one plane from the next is fixed at a predetermined value. It is then not important that each seed of one plane lie above or below a corresponding seed of the adjacent plane, since the whole plane moves in unison. The seeds are always approximately the same distance apart. This does not rely on the needles being parallel.

The present device is distinguishable over the prior art in several respects. The novel aspects of a planar distribution disposes of the problems of parallel insertions encountered in other devices. In addition, the present device allows the insertion of multiple seeds by one application, which results in greater ease and efficiency of application. Moreover, the array of needles can be increased or decreased to insert a greater or lesser number of seeds depending upon the size or volume of the tumor.

The above mentioned and other features of this invention and the manner of obtaining them will become more apparent, and the invention itself will be best understood by reference to the following description of an embodiment of the invention taken in conjunction with the accompanying drawings wherein:

FIG. 1 is a side perspective view of the planar seed applicator;

FIG. 2 is an exploded frontal view of the device shown in FIG. 1;

FIG. 3 is a cross sectional view of the device shown in FIG. 1;

FIG. 4 is a top plan view of the array of needles and steel plate shown in FIG. 1;

FIG. 5 is a detailed cross sectional view of the device shown in FIG. 1.

The device comprises an array of hollow stainless #17 gauge steel needles 6 spaced approximately 1 cm. apart and approximately 2.6 cm. in length stabilized on a stainless steel plate 3. The tips of needles 6 are pointed to permit ease of insertion through skin tissue. A similar array of solid rods or trochars 7 of stainless steel fits inside the needles 6 and is stabilized on a similar stainless steel plate 1. A spacer 2 approximately 7.5 mm. in height is inserted between the plates to keep the trochars steady in the needles 6 while the needles are being inserted into the tumor. A set of teflon spacers 4, 5 from 0.25 cm. to 2 cm. in height, is placed over the needles 6 to allow shallower planes of seeds to be inserted.

Using this device, one radioactive seed is inserted into each needle 6 and the array is inserted into the tumor. The array of trochars 7 is inserted to push out the seeds at a fixed depth, thus creating a plane of seeds in the tumor. A spacer 5 is then placed over the needles and the process repeated to give a plane of seeds at a more superficial depth than the previous plane.

The device allows the needles 6 to be pre-loaded with a seed and sealed with "bone-wax". The trochars 7 do not push the seeds out of the needle 6 until the spacer 2 is removed. This spacer has a hole in the one end to allow a thread attachment at the time of the operation. This aids in the removal of the spacer 2 when the needles 6 are at their correct detph and the seeds are to be pushed out.

In its preferred embodiment, the device is operated as following:

Choose an array of needles 6 large enough to cover the tumor (more than one array may be needed);

Estimate the depth of the tumor and set the needle length so that the deepest seeds will lie at the deepest aspect of the tumor;

Load the seeds into the needles 6 with the trochars 7 in place and threaded spacer 2 between the plates 1, 3;

Seal tips of the needles 6 with "bone-wax";

Insert the needle array into the tumor with a finger at the deep aspect of the tumor to feel for the tips of the needles 6 and ensure they are at the correct depth;

Remove the spacer 2 from between the steel plates 1, 3 by means of the thread;

Close the two plates 1, 3 by pressure from above and thereby drop out a set of seeds into the deep plane;

Remove the needles 6 and trochars 7 with the plates 1, 3 in the closed or seeds-out position;

Choose the distance between the planes which is dependent on the strength of the seeds used and the radiation dose required; and Place the chosen spacer 4, 5 over the needles 6 and against the base plate 3, repeating the process.

EXAMPLES

The invention has been used as described above in three patients. One patient had carcinoma of the floor of the mouth with a metastises to a neck node. Two others had prostatic carcinoma. In all three patients, use of the device resulted in the desired spatial distribution of radioactive seeds. Good response was achieved in all three patients in the treated areas.

Those who are skilled in the art will perceive how modifications may be made in the disclosed structure. Therefore, the appended claims are to be construed to cover all equivalent structures that may fall within the true scope and spirit of the invention.

I claim:

1. A radioactive seed applicator for implanting radioactive seed material in a planar array below the skin surface comprising:
   a first stablizing structure;
   a plurality of spaced-apart hollow needles extending from said first stablizing structure, said needles having tips arranged in a planar configuration;
   a matching array of spaced-apart trochars disposed for movement within said hollow needles whereby radioactive seed material disposed in said hollow needles is forced through said needles and implanted in a planar array at a predetermined depth below the skin surface when said needles are inserted through the skin.

2. The applicator of claim 1 wherein said radioactive seed material is radioactive Iodine, $^{125}$I.

3. The applicator of claim 1 wherein said matching array of spaced-apart trochars extends from a second stablizing structure.

4. The applicator of claim 3 wherein removable spacer means are disposed between said first and second stablizing structures to keep said array of trochars steady in said hollow needles while said needles are inserted through said skin surface, said spacer means being removed after said needles are inserted through said skin to permit said array of trochars to force said radioactive seed material out of said needles in a planar configuration.

5. The applicator of claim 1 including at least one additional removable spacer means disposed between the tips of said hollow needles and said first stablizing structure to allow insertion of said needles at predetermined variable depths beneath a skin surface, said depths bearing a direct relationship to the thickness of said additional spacer means.

* * * * *